(12) United States Patent
McNiven et al.

(10) Patent No.: US 10,238,494 B2
(45) Date of Patent: Mar. 26, 2019

(54) SELF-ALIGNING RADIOPAQUE RING

(71) Applicant: Evalve, Inc., Menlo Park, CA (US)

(72) Inventors: Sean A. McNiven, Menlo Park, CA (US); Herminia C. Heflin, Pleasanton, CA (US); Stephanie A. Kozuma, San Mateo, CA (US)

(73) Assignee: EVALVE, INC., Santa Clara, CA (US)

( * ) Notice: Subject to any disclaimer, the term of this patent is extended or adjusted under 35 U.S.C. 154(b) by 96 days.

(21) Appl. No.: 14/754,274

(22) Filed: Jun. 29, 2015

(65) Prior Publication Data

US 2016/0374811 A1    Dec. 29, 2016

(51) Int. Cl.
 *A61F 2/24* (2006.01)
 *A61B 19/00* (2006.01)
 *A61B 90/00* (2016.01)
 *A61B 17/00* (2006.01)

(52) U.S. Cl.
 CPC ............ *A61F 2/2466* (2013.01); *A61B 90/39* (2016.02); *A61F 2/246* (2013.01); *A61B 2017/00238* (2013.01); *A61B 2090/3966* (2016.02)

(58) Field of Classification Search
 CPC .... A61F 2/2427; A61F 2/2439; A61F 2/2466; A61F 2/246; A61B 90/39
 See application file for complete search history.

(56) References Cited

U.S. PATENT DOCUMENTS

| | | |
|---|---|---|
| 2,097,018 A | 10/1937 | Chamberlain |
| 2,108,206 A | 2/1938 | Meeker |
| 3,296,668 A | 1/1967 | Aiken |
| 3,378,010 A | 4/1968 | Codling et al. |
| 3,557,780 A | 1/1971 | Sato |
| 3,675,639 A | 7/1972 | Cimber |
| 3,874,388 A | 4/1975 | King et al. |
| 4,007,743 A | 2/1977 | Blake |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,425,908 A | 1/1984 | Simon |
| 4,458,682 A | 7/1984 | Cerwin |
| 4,487,205 A | 12/1984 | Di Giovanni et al. |
| 4,498,476 A | 2/1985 | Cerwin et al. |

(Continued)

FOREIGN PATENT DOCUMENTS

| | | |
|---|---|---|
| CN | 102258402 | 11/2014 |
| DE | 3504292 | 7/1986 |

(Continued)

OTHER PUBLICATIONS

U.S. Appl. No. 14/216,787, filed Mar. 17, 2014, Basude et al.

(Continued)

*Primary Examiner* — Tuan V Nguyen
(74) *Attorney, Agent, or Firm* — Workman Nydegger

(57) ABSTRACT

An intravascular device configured to be recaptured within a guide catheter has a ring located at the distal end of a delivery catheter. The ring has an outer diameter greater than that of the delivery catheter and a sloped guide surface near the outer edge of the ring to urge the ring and delivery catheter toward a radially centered position within the guide catheter.

9 Claims, 7 Drawing Sheets

(56) References Cited

U.S. PATENT DOCUMENTS

| | | | |
|---|---|---|---|
| 4,510,934 A | 4/1985 | Batra | |
| 4,531,522 A | 7/1985 | Bedi et al. | |
| 4,578,061 A | 3/1986 | Lemelson | |
| 4,641,366 A | 2/1987 | Yokoyama et al. | |
| 4,686,965 A | 8/1987 | Bonnet et al. | |
| 4,777,951 A | 10/1988 | Cribier et al. | |
| 4,809,695 A | 3/1989 | Gwathmey et al. | |
| 4,896,986 A | 1/1990 | Terayama | |
| 4,944,295 A | 7/1990 | Gwathmey et al. | |
| 4,969,890 A | 11/1990 | Sugita et al. | |
| 5,015,249 A | 5/1991 | Nakao et al. | |
| 5,019,096 A | 5/1991 | Fox, Jr. et al. | |
| 5,042,161 A * | 8/1991 | Hodge | A61B 5/1076 33/501.45 |
| 5,042,707 A | 8/1991 | Taheri | |
| 5,047,041 A | 9/1991 | Samuels | |
| 5,049,153 A | 9/1991 | Nakao et al. | |
| 5,061,277 A | 10/1991 | Carpentier et al. | |
| 5,069,679 A | 12/1991 | Taheri | |
| 5,108,368 A | 4/1992 | Hammerslag et al. | |
| 5,125,758 A | 6/1992 | DeWan | |
| 5,171,252 A | 12/1992 | Friedland | |
| 5,171,259 A | 12/1992 | Inoue | |
| 5,190,554 A | 3/1993 | Coddington et al. | |
| 5,195,968 A | 3/1993 | Lundquist et al. | |
| 5,209,756 A | 5/1993 | Seedhom et al. | |
| 5,226,429 A | 7/1993 | Kuzmak | |
| 5,226,911 A | 7/1993 | Chee et al. | |
| 5,234,437 A | 8/1993 | Sepetka | |
| 5,236,450 A * | 8/1993 | Scott | A61F 2/0095 623/2.11 |
| 5,242,456 A | 9/1993 | Nash et al. | |
| 5,250,071 A | 10/1993 | Palermo | |
| 5,251,611 A | 10/1993 | Zehel et al. | |
| 5,254,130 A | 10/1993 | Poncet et al. | |
| 5,261,916 A | 11/1993 | Engelson | |
| 5,263,939 A | 11/1993 | Wortrich | |
| 5,271,381 A | 12/1993 | Ailinger et al. | |
| 5,275,578 A | 1/1994 | Adams | |
| 5,282,845 A | 2/1994 | Bush et al. | |
| 5,304,131 A | 4/1994 | Paskar | |
| 5,306,283 A | 4/1994 | Conners | |
| 5,306,286 A | 4/1994 | Stack et al. | |
| 5,312,415 A | 5/1994 | Palermo | |
| 5,314,424 A | 5/1994 | Nicholas | |
| 5,318,525 A | 6/1994 | West et al. | |
| 5,320,632 A | 6/1994 | Heidmueller | |
| 5,325,845 A | 7/1994 | Adair | |
| 5,330,442 A | 7/1994 | Green et al. | |
| 5,342,393 A | 8/1994 | Stack | |
| 5,350,397 A | 9/1994 | Palermo et al. | |
| 5,350,399 A | 9/1994 | Erlebacher et al. | |
| 5,359,994 A | 11/1994 | Krauter et al. | |
| 5,368,564 A | 11/1994 | Savage | |
| 5,368,601 A | 11/1994 | Sauer et al. | |
| 5,383,886 A | 1/1995 | Kensey et al. | |
| 5,391,182 A | 2/1995 | Chin | |
| 5,403,312 A | 4/1995 | Yates et al. | |
| 5,403,326 A | 4/1995 | Harrison et al. | |
| 5,405,402 A * | 4/1995 | Dye | A61F 2/30724 623/22.38 |
| 5,417,699 A | 5/1995 | Klein et al. | |
| 5,417,700 A | 5/1995 | Egan | |
| 5,423,857 A | 6/1995 | Rosenman et al. | |
| 5,423,858 A | 6/1995 | Bolanos et al. | |
| 5,423,882 A | 6/1995 | Jackman et al. | |
| 5,431,666 A | 7/1995 | Sauer et al. | |
| 5,437,551 A | 8/1995 | Chalifoux | |
| 5,437,681 A | 8/1995 | Meade et al. | |
| 5,447,966 A | 9/1995 | Hermes et al. | |
| 5,450,860 A | 9/1995 | O'Connor | |
| 5,456,400 A | 10/1995 | Shichman et al. | |
| 5,456,684 A | 10/1995 | Schmidt et al. | |
| 5,462,527 A | 10/1995 | Stevens-Wright et al. | |
| 5,464,394 A | 11/1995 | Miller et al. | |
| 5,472,044 A | 12/1995 | Hall et al. | |
| 5,476,470 A | 12/1995 | Fitzgibbons, Jr. | |
| 5,477,856 A | 12/1995 | Lundquist | |
| 5,478,309 A | 12/1995 | Sweezer et al. | |
| 5,478,353 A | 12/1995 | Yoon | |
| 5,487,746 A | 1/1996 | Yu et al. | |
| 5,489,296 A * | 2/1996 | Love | A61F 2/2496 600/587 |
| 5,496,332 A | 3/1996 | Sierra et al. | |
| 5,507,725 A | 4/1996 | Savage et al. | |
| 5,507,755 A | 4/1996 | Gresl et al. | |
| 5,507,757 A | 4/1996 | Sauer et al. | |
| 5,520,701 A | 5/1996 | Lerch | |
| 5,522,873 A | 6/1996 | Jackman et al. | |
| 5,527,313 A | 6/1996 | Scott et al. | |
| 5,527,321 A | 6/1996 | Hinchliffe | |
| 5,527,322 A | 6/1996 | Klein et al. | |
| 5,536,251 A | 7/1996 | Evard et al. | |
| 5,540,705 A | 7/1996 | Meade et al. | |
| 5,542,949 A | 8/1996 | Yoon | |
| 5,562,678 A | 10/1996 | Booker | |
| 5,569,274 A | 10/1996 | Rapacki et al. | |
| 5,571,085 A | 11/1996 | Accisano, III | |
| 5,571,137 A | 11/1996 | Marlow et al. | |
| 5,571,215 A | 11/1996 | Sterman et al. | |
| 5,575,802 A | 11/1996 | McQuilkin et al. | |
| 5,582,611 A | 12/1996 | Tsuruta et al. | |
| 5,593,424 A | 1/1997 | Northrup, III | |
| 5,593,435 A | 1/1997 | Carpentier et al. | |
| 5,609,598 A | 3/1997 | Laufer et al. | |
| 5,618,306 A | 4/1997 | Roth et al. | |
| 5,620,452 A | 4/1997 | Yoon | |
| 5,620,461 A | 4/1997 | Mugs Van De Moer et al. | |
| 5,626,588 A | 5/1997 | Sauer et al. | |
| 5,630,832 A | 5/1997 | Giordano et al. | |
| 5,634,932 A | 6/1997 | Schmidt | |
| 5,636,634 A | 6/1997 | Kordis et al. | |
| 5,639,277 A | 6/1997 | Mariant et al. | |
| 5,640,955 A | 6/1997 | Ockuly et al. | |
| 5,649,937 A | 7/1997 | Bito et al. | |
| 5,662,606 A | 9/1997 | Cimino et al. | |
| 5,662,681 A | 9/1997 | Nash et al. | |
| 5,669,917 A | 9/1997 | Sauer et al. | |
| 5,690,671 A | 11/1997 | McGurk et al. | |
| 5,695,504 A | 12/1997 | Gifford, III et al. | |
| 5,695,505 A | 12/1997 | Yoon | |
| 5,702,825 A | 12/1997 | Keita et al. | |
| 5,706,824 A | 1/1998 | Whittier | |
| 5,709,707 A | 1/1998 | Lock et al. | |
| 5,713,910 A | 2/1998 | Gordon et al. | |
| 5,713,911 A | 2/1998 | Racene et al. | |
| 5,715,817 A | 2/1998 | Stevens-Wright et al. | |
| 5,716,367 A | 2/1998 | Koike et al. | |
| 5,718,714 A | 2/1998 | Livneh | |
| 5,719,725 A | 2/1998 | Nakao | |
| 5,722,421 A | 3/1998 | Francese et al. | |
| 5,725,542 A | 3/1998 | Yoon | |
| 5,725,556 A | 3/1998 | Moser et al. | |
| 5,738,649 A | 4/1998 | Macoviak | |
| 5,741,280 A | 4/1998 | Fleenor | |
| 5,741,286 A | 4/1998 | Recuset | |
| 5,749,828 A | 5/1998 | Solomon et al. | |
| 5,759,193 A | 6/1998 | Burbank et al. | |
| 5,769,863 A | 6/1998 | Garrison | |
| 5,772,578 A | 6/1998 | Heimberger et al. | |
| 5,782,845 A | 7/1998 | Shewchuk | |
| 5,797,927 A | 8/1998 | Yoon | |
| 5,810,847 A | 9/1998 | Laufer et al. | |
| 5,810,849 A | 9/1998 | Kontos | |
| 5,810,853 A | 9/1998 | Yoon | |
| 5,810,876 A | 9/1998 | Kelleher | |
| 5,814,029 A | 9/1998 | Hassett | |
| 5,820,592 A | 10/1998 | Hammerslag | |
| 5,820,631 A | 10/1998 | Nobles | |
| 5,823,955 A | 10/1998 | Kuck et al. | |
| 5,824,065 A | 10/1998 | Gross | |
| 5,827,237 A | 10/1998 | Macoviak et al. | |
| 5,833,671 A | 11/1998 | Macoviak et al. | |
| 5,836,955 A | 11/1998 | Buelna et al. | |

(56) References Cited

U.S. PATENT DOCUMENTS

| | | |
|---|---|---|
| 5,843,031 A | 12/1998 | Hermann et al. |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,860,990 A | 1/1999 | Nobles et al. |
| 5,861,003 A | 1/1999 | Latson et al. |
| 5,868,733 A | 2/1999 | Ockuly et al. |
| 5,871,493 A | 2/1999 | Sjostrom et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,902,290 A | 5/1999 | Peacock, III et al. |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,964,717 A | 10/1999 | Gottlieb et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 5,993,470 A | 11/1999 | Yoon |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,036,699 A | 3/2000 | Andreas et al. |
| 6,048,351 A | 4/2000 | Gordon et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fenton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,139,214 A | 10/2000 | Zirps et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,182,664 B1 | 2/2001 | Cosgrove |
| 6,187,003 B1 | 2/2001 | Buysse et al. |
| 6,190,408 B1 | 2/2001 | Melvin |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,350,281 B1 * | 2/2002 | Rhee ............... A61B 5/1076 33/512 |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen, III et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |

(56) References Cited

U.S. PATENT DOCUMENTS

| | | |
|---|---|---|
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 8,216,256 B2 | 7/2012 | Raschdorf, Jr. et al. |
| D668,334 S | 10/2012 | Makowski et al. |
| D740,414 S | 10/2015 | Katsura |
| D809,139 S | 1/2018 | Marsot et al. |
| 2001/0004715 A1 | 6/2001 | Duran et al. |
| 2001/0005787 A1 | 6/2001 | Oz et al. |
| 2001/0007067 A1 | 7/2001 | Kurfess et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0181855 A1 | 9/2003 | Simpson et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | MacHold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138529 A1 | 7/2004 | Wiltshire et al. |
| 2004/0138675 A1 | 7/2004 | Crabtree |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243227 A1 | 12/2004 | Starksen et al. |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0006432 A1 | 1/2005 | Racenet et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0009715 A1 | 1/2006 | Khairkhahan et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |

(56) References Cited

U.S. PATENT DOCUMENTS

| | | | |
|---|---|---|---|
| 2006/0058871 A1 | 3/2006 | Zakay et al. | |
| 2006/0064115 A1 | 3/2006 | Allen et al. | |
| 2006/0064116 A1 | 3/2006 | Allen et al. | |
| 2006/0064118 A1 | 3/2006 | Kimblad | |
| 2006/0089671 A1 | 4/2006 | Goldfarb et al. | |
| 2006/0089711 A1 | 4/2006 | Dolan | |
| 2006/0135993 A1 | 6/2006 | Seguin | |
| 2006/0184203 A1 | 8/2006 | Martin et al. | |
| 2006/0195012 A1 | 8/2006 | Mortier et al. | |
| 2006/0229708 A1 | 10/2006 | Powell et al. | |
| 2006/0252984 A1 | 11/2006 | Randert et al. | |
| 2006/0287643 A1 | 12/2006 | Perlin | |
| 2007/0038293 A1 | 2/2007 | St. Goar et al. | |
| 2007/0088277 A1 | 4/2007 | McGinley et al. | |
| 2007/0088431 A1 | 4/2007 | Bourang et al. | |
| 2007/0100356 A1 | 5/2007 | Lucatero et al. | |
| 2007/0118155 A1 | 5/2007 | Goldfarb et al. | |
| 2007/0129737 A1 | 6/2007 | Goldfarb et al. | |
| 2007/0198082 A1 | 8/2007 | Kapadia et al. | |
| 2008/0039935 A1 | 2/2008 | Buch et al. | |
| 2008/0051703 A1 | 2/2008 | Thorton et al. | |
| 2008/0051807 A1 | 2/2008 | St. Goar et al. | |
| 2008/0097489 A1 | 4/2008 | Goldfarb et al. | |
| 2008/0154299 A1 | 6/2008 | Livneh | |
| 2008/0167714 A1 | 7/2008 | St. Goer et al. | |
| 2008/0183194 A1 | 7/2008 | Goldfarb et al. | |
| 2009/0143851 A1* | 6/2009 | Paul, Jr. | A61M 29/02 623/1.11 |
| 2009/0156995 A1 | 6/2009 | Martin et al. | |
| 2009/0177266 A1 | 7/2009 | Powell et al. | |
| 2009/0198322 A1 | 8/2009 | Deem et al. | |
| 2009/0270858 A1 | 10/2009 | Hauck et al. | |
| 2009/0326567 A1 | 12/2009 | Goldfarb et al. | |
| 2010/0016958 A1 | 1/2010 | St. Goer et al. | |
| 2010/0168717 A1 | 7/2010 | Grasse et al. | |
| 2010/0217184 A1 | 8/2010 | Koblish et al. | |
| 2010/0252293 A1 | 10/2010 | Lopano et al. | |
| 2011/0077498 A1 | 3/2011 | McDaniel | |
| 2011/0190778 A1 | 8/2011 | Arpasi et al. | |
| 2012/0089136 A1 | 4/2012 | Levin et al. | |
| 2012/0253329 A1 | 10/2012 | Zemlok et al. | |
| 2012/0330408 A1* | 12/2012 | Hillukka | A61F 2/0095 623/2.11 |
| 2013/0053822 A1 | 2/2013 | Fischell et al. | |
| 2013/0066342 A1 | 3/2013 | Dell et al. | |
| 2013/0304117 A1 | 11/2013 | Sugiyama | |
| 2013/0310813 A1 | 11/2013 | Kaercher et al. | |
| 2014/0012287 A1 | 1/2014 | Oyola et al. | |
| 2014/0025103 A1 | 1/2014 | Hundertmark et al. | |
| 2014/0148651 A1 | 5/2014 | Aman et al. | |
| 2014/0148673 A1 | 5/2014 | Bogusky | |
| 2014/0171923 A1 | 6/2014 | Aranyi | |
| 2014/0196923 A1 | 7/2014 | Leupert et al. | |
| 2014/0243969 A1 | 8/2014 | Venkatasubramanian et al. | |
| 2015/0060516 A1 | 3/2015 | Collings et al. | |
| 2015/0182334 A1 | 7/2015 | Bourang et al. | |
| 2015/0306806 A1 | 10/2015 | Dando et al. | |
| 2016/0174979 A1 | 6/2016 | Wei | |
| 2016/0367787 A1 | 12/2016 | Van Hoven et al. | |
| 2017/0035566 A1 | 2/2017 | Krone et al. | |
| 2017/0100250 A1 | 4/2017 | Marsot et al. | |

FOREIGN PATENT DOCUMENTS

| | | |
|---|---|---|
| DE | 10116168 | 11/2001 |
| EP | 0179562 | 7/1989 |
| EP | 0558031 | 2/1993 |
| EP | 0684012 | 11/1995 |
| EP | 0727239 | 8/1996 |
| EP | 0782836 | 7/1997 |
| EP | 0990449 | 4/2000 |
| EP | 1230899 | 8/2002 |
| EP | 1674040 | 6/2006 |
| EP | 2465568 | 6/2012 |
| FR | 2768324 | 3/1999 |
| GB | 1598111 | 9/1981 |
| GB | 2151142 | 7/1985 |
| GB | 2222951 | 3/1990 |
| JP | H 09253030 | 9/1997 |
| JP | H 11089937 | 4/1999 |
| JP | 2000283130 | 10/2000 |
| JP | 2015502548 | 1/2015 |
| WO | WO 1981000668 | 3/1981 |
| WO | WO 1991018881 | 12/1991 |
| WO | WO 1992012690 | 8/1992 |
| WO | WO 1994018881 | 9/1994 |
| WO | WO 1994018893 | 9/1994 |
| WO | WO 1995011620 | 5/1995 |
| WO | WO 1995015715 | 6/1995 |
| WO | WO 1996014032 | 5/1996 |
| WO | WO 1996020655 | 7/1996 |
| WO | WO 1996022735 | 8/1996 |
| WO | WO 1996030072 | 10/1996 |
| WO | WO 1997018746 | 5/1997 |
| WO | WO 1997025927 | 7/1997 |
| WO | WO 1997026034 | 7/1997 |
| WO | WO 1997038748 | 10/1997 |
| WO | WO 1997039688 | 10/1997 |
| WO | WO 1997048436 | 12/1997 |
| WO | WO 1998007375 | 2/1998 |
| WO | WO 1998024372 | 6/1998 |
| WO | WO 1998030153 | 7/1998 |
| WO | WO 1998032382 | 7/1998 |
| WO | WO 1999007354 | 2/1999 |
| WO | WO 1999013777 | 3/1999 |
| WO | WO 1999066967 | 12/1999 |
| WO | WO 2000002489 | 1/2000 |
| WO | WO 2000003651 | 1/2000 |
| WO | WO 2000012168 | 3/2000 |
| WO | WO 2000044313 | 8/2000 |
| WO | WO 2000059382 | 10/2000 |
| WO | WO 2001000111 | 1/2001 |
| WO | WO 2001000114 | 1/2001 |
| WO | WO 2001003651 | 1/2001 |
| WO | WO 2001026557 | 4/2001 |
| WO | WO 2001026586 | 4/2001 |
| WO | WO 2001026587 | 4/2001 |
| WO | WO 2001026588 | 4/2001 |
| WO | WO 2001026703 | 4/2001 |
| WO | WO 2001028432 | 4/2001 |
| WO | WO 2001028455 | 4/2001 |
| WO | WO 2001047438 | 7/2001 |
| WO | WO 2001049213 | 7/2001 |
| WO | WO 2001050985 | 7/2001 |
| WO | WO 2001054618 | 8/2001 |
| WO | WO 2001056512 | 8/2001 |
| WO | WO 2001066001 | 9/2001 |
| WO | WO 2001070320 | 9/2001 |
| WO | WO 2001089440 | 11/2001 |
| WO | WO 2001095831 | 12/2001 |
| WO | WO 2001095832 | 12/2001 |
| WO | WO 2001097741 | 12/2001 |
| WO | WO 2002000099 | 1/2002 |
| WO | WO 2002001999 | 1/2002 |
| WO | WO 2002003892 | 1/2002 |
| WO | WO 2002034167 | 5/2002 |
| WO | WO 2002060352 | 8/2002 |
| WO | WO 2002062263 | 8/2002 |
| WO | WO 2002062270 | 8/2002 |
| WO | WO 2002062408 | 8/2002 |
| WO | WO 2003001893 | 1/2003 |
| WO | WO 2003003930 | 1/2003 |
| WO | WO 2003020179 | 3/2003 |
| WO | WO 2003028558 | 4/2003 |
| WO | WO 2003037171 | 5/2003 |
| WO | WO 2003047467 | 6/2003 |
| WO | WO 2003049619 | 6/2003 |
| WO | WO 2003073910 | 9/2003 |
| WO | WO 2003073913 | 9/2003 |
| WO | WO 2003082129 | 10/2003 |
| WO | WO 2003105667 | 12/2003 |
| WO | WO 2004004607 | 1/2004 |
| WO | WO 2004012583 | 2/2004 |

(56) References Cited

FOREIGN PATENT DOCUMENTS

| | | |
|---|---|---|
| WO | WO 2004012789 | 2/2004 |
| WO | WO 2004014282 | 2/2004 |
| WO | WO 2004019811 | 3/2004 |
| WO | WO 2004030570 | 4/2004 |
| WO | WO 2004037317 | 5/2004 |
| WO | WO 2004045370 | 6/2004 |
| WO | WO 2004045378 | 6/2004 |
| WO | WO 2004045463 | 6/2004 |
| WO | WO 2004047679 | 6/2004 |
| WO | WO 2004062725 | 7/2004 |
| WO | WO 2004082523 | 9/2004 |
| WO | WO 2004082538 | 9/2004 |
| WO | WO 2004093730 | 11/2004 |
| WO | WO 2004103162 | 12/2004 |
| WO | WO 2004112585 | 12/2004 |
| WO | WO 2004112651 | 12/2004 |
| WO | WO 2005002424 | 1/2005 |
| WO | WO 2005018507 | 3/2005 |
| WO | WO 2005027797 | 3/2005 |
| WO | WO 2005032421 | 4/2005 |
| WO | WO 2005062931 | 7/2005 |
| WO | WO 2005112792 | 12/2005 |
| WO | WO 2006037073 | 4/2006 |
| WO | WO 2006105008 | 10/2006 |
| WO | WO 2006105009 | 10/2006 |
| WO | WO 2006115875 | 11/2006 |
| WO | WO 2006115876 | 11/2006 |
| WO | WO 2007047488 | 4/2007 |
| WO | WO 2008031103 | 3/2008 |
| WO | WO 2014182797 | 11/2014 |
| WO | WO 2015061052 | 4/2015 |
| WO | WO 2016204954 | 12/2016 |
| WO | WO 2017/003606 | 1/2017 |
| WO | WO 2017023534 | 2/2017 |

OTHER PUBLICATIONS

U.S. Appl. No. 15/662,084, filed Jul. 27, 2017, Prabhu et al.
U.S. Appl. No. 29/633,930, filed Jan. 17, 2018, Marsot et al.
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitrel valve repair: a simple solution for complex problems," Journal of Thoracic and Cardiovascular Surgery, 122:674-681 (2001).
Alfieri et al., "The edge to edge technique," The European Association for Cardio-Thoracic Surgery 14th Annual Meeting, Oct. 7-11, 2000, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Arisi et al., "Mitral Valve Repair with Alfieri Technique in Mitral Regurgitation of Diverse Etiology: Early Echocardiographic Results," Circulation Supplement II, 104(17):3240 (2001).
Bailey, "Mitral Regurgitation" in Surgery of the Heart, Chapter 20, pp. 686-737 (1955).
Bernal et al., "The Valve Racket': a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Filsoufi et al., "Restoring Optimal Surface of Coaptation With a Mini Leaflet Prosthesis: A New Surgical Concept for the Correction of Mitral Valve Prolapse," Intl. Soc. For Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172-175.
Gatti et al., "The edge to edge technique as a trick to rescue an imperfect mitral valve repair," J. Eur. Cardiothorac Surg, 22:817-820 (2002).
Gillinov et al., "Is Minimally Invasive Heart Valve Surgery a Paradigm for the Future?" Current Cardiology Reports, 1:318-322 (1999).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion of PCT Application No. PCT/US2009/068023, dated Mar. 2, 2010, 10 pages total.
Izzat et al., "Early Experience with Partial Left Ventriculectomy in the Asia-Pacific Region," Annuals of Thoracic Surgery, 67:1703-1707 (1999).
Kallner et al., "Transaortic Approach for the Alfieri Stitch," Ann Thorac Surg, 71:378-380 (2001).
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Kherani et al., "The Edge-To-Edge Mitral Valve Repair: The Columbia Presbyterian Experience," Ann. Thorac. Surg., 78:73-76 (2004).

(56) References Cited

OTHER PUBLICATIONS

Konertz et al., "Results After Partial Left Ventriculectomy in a European Heart Failure Population," Journal of Cardiac Surgery, 14:129-135 (1999).
Kron et al., "Surgical Relocation of the Posterior Papillary Muscle in Chronic Ischemic Mitral Regurgitation," Annals. Of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "'Double-Orifice' Technique to Repair Extensive Mitral Valve Excision Following Acute Endocarditis," J. Card Surg, 13:24-26 (1998).
Lorusso et al., "The double-orifice technique for mitral valve reconstruction: predictors of postoperative outcome," Eur J. Cardiothorac Surg, 20:583-589 (2001).
Maisano et al., "The double orifice repair for Barlow Disease: a simple solution for a complex repair," Supplement I Circulation, (Nov. 1999); 100(18):1-94.
Maisano et al., "The double orifice technique as a standardized approach to treat mitral regurgitation due to severe myxomatous disease: surgical technique," European Journal of Cardio-thoracic Surgery, 17:201-205 (2000).
Maisano et al., "The hemodynamic effects of double-orifice valve repair for mitral regurgitation: 3D computational model," European Journal of Cardio-thoracic Surgery, 15:419-425 (1999).
Maisano et al., "Valve repair for traumatic tricuspid regurgitation," Eur. J. Cardio-thorac Surg, 10:867-873 (1996).
Mantovani et al., "Edge-to-edge Repair of Congenital Familiar Tricuspid Regurgitation: Case Report," J. Heart Valve Dis., 9:641-643 (2000).
McCarthy et al., "Partial left ventriculectomy and mitral valve repair for end-stage congestive heart failure," European Journal of Cardio-thoracic Surgery, 13:337-343 (1998).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Noera et al., "Tricuspid Valve Incompetence Caused by Nonpenetrating Thoracic Trauma", Annals of Thoracic Surgery, 51:320-322 (1991).
Osawa et al., "Partial Left Ventriculectomy in a 3-Year Old Boy with Dilated Cardiomyopathy," Japanese Journal of Thoracic and Cardiovascular Surg, 48:590-593 (2000).
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Robicsek et al., #60 The Bicuspid Aortic Valve: How Does It Function? Why Does It Fail? 2003 STS Presentation, [Abstract Only].
Supplemental European Search Report of EP Application No. 02746781, dated May 13, 2008, 3 pages total.
Supplementary European Search Report issued in European Application No. 05753261.6 dated Jun. 9, 2011, 3 pages total.
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
Umana et al., "'Bow-tie' Mitral Valve Repair Successfully Addresses Subvalvular Dysfunction in Ischemic Mitral Regurgitation," Surgical Forum, XLVIII:279-280 (1997).
Votta et al., "3-D Computational Analysis of the Stress Distribution on the Leaflets after Edge-to-Edge Repair of Mitral Regurgitation," Journal of Heart Valve Disease, 11:810-822 (2002).
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 14/744,415, Nov. 22, 2017, Office Action.
U.S. Appl. No. 14/744,415, Jun. 1, 2018, Office Action.
U.S. Appl. No. 14/820,141, Jan. 25, 2019, Office Action.
U.S. Appl. No. 14/820,141, Sep. 5, 2018, Office Action.
U.S. Appl. No. 14/820,141, Oct. 30, 2018, Interview Summary.
U.S. Appl. No. 14/879,726, Oct. 2, 2017, Office Action.
U.S. Appl. No. 14/879,726, Apr. 20, 2018, Office Action.
U.S. Appl. No. 14/879,726, Sep. 5, 2018, Notice of Allowance.
U.S. Appl. No. 14/879,726, Nov. 8, 2018, Notice of Allowance.
U.S. Appl. No. 29/505,404, Jan. 3, 2017, Office Action.
U.S. Appl. No. 29/505,404, Mar. 30, 2017, Office Action.
U.S. Appl. No. 29/505,404, Sep. 26, 2017, Notice of Allowance.

* cited by examiner

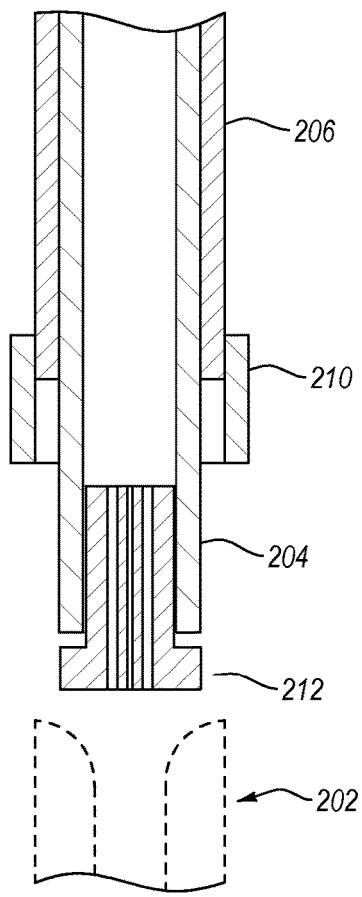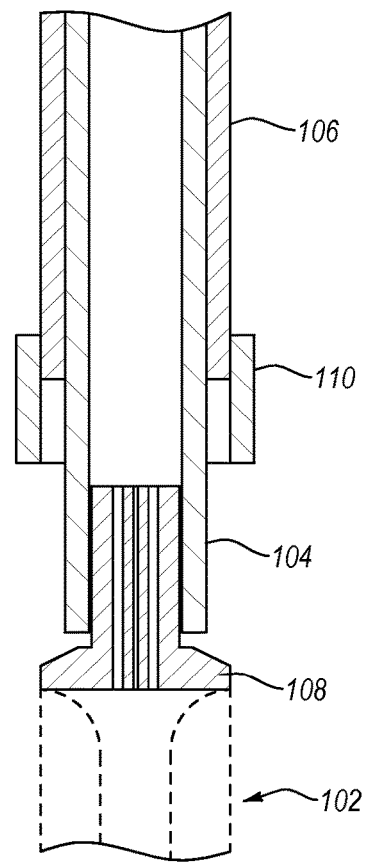
FIG. 3
FIG. 4

SELF-ALIGNING RADIOPAQUE RING

BACKGROUND OF THE DISCLOSURE

Intravascular medical procedures allow the performance of therapeutic treatments in a variety of locations within a patient's body while requiring only relatively small access incisions. An intravascular procedure may, for example, eliminate the need for open-heart surgery, reducing risks, costs, and time associated with an open-heart procedure. The intravascular procedure also enables faster recovery times with lower associated costs and risks of complication. An example of an intravascular procedure that significantly reduces procedure and recovery time and cost over conventional open surgery is a heart valve replacement or repair procedure. An artificial valve is guided to the heart through the patient's vasculature. For example, a catheter is inserted into the patient's vasculature and directed to the inferior vena cava. The catheter is then urged through the inferior vena cava toward the heart by applying force longitudinally to the catheter. Upon entering the heart from the inferior vena cava, the catheter enters the right atrium. In a procedure to repair a mitral valve using a mitral clip, the left atrium must be reached for the catheter to access the mitral valve of the heart. The catheter may reach the left atrium through a puncture in the intra-atrial septum. To do so, the distal end of the catheter may be deflected by one or more wires positioned inside the catheter. Precise control of the distal end of the catheter allows for smaller punctures in the intra-atrial septum, more reliable and faster positioning of a mitral clip on the mitral valve, and other improvements in the procedures.

The mitral clip needs to be placed precisely relative to the mitral valve. Once in place, the mitral clip is difficult to move or replace, so an accurate initial placement during the procedure is preferred. Imaging of the mitral clip and the catheter that delivers the mitral clip to the mitral valve in the heart is needed. Additionally, the ability to recapture a partially deployed mitral clip is desirable in the event that the distal end of the catheter and moves relative to the mitral valve and compromises the precise positioning of the mitral clip.

The recapture of the mitral clip requires the collapse of one or more moveable arms of the mitral clip. The one or more moveable arms move toward the axis of a catheter steerable guide catheter ("SGC") and the mitral clip may be retracted or recaptured into the tip of the SGC to allow replacement and/or redeployment of the mitral clip. In some instances, the one or more moveable arms of the mitral clip may contact the tip or other portion of the exterior of the SGC and limit or prevent recapture. A more reliable recapture device and/or method may reduce complications and potential harm to the patient.

BRIEF SUMMARY OF THE DISCLOSURE

This summary is provided to introduce a selection of concepts that are further described below in the detailed description. This summary is not intended to identify specific features of the claimed subject matter, nor is it intended to be used as an aid in limiting the scope of the claimed subject matter.

In a first embodiment, a device for aligning components of an intravascular system includes a head and a body with a longitudinal axis extending therethrough. The body is connected proximally to the head and has a body radius. The head has a face with a face radius. A face radius to body radius ratio is in a range of 1.20 to 1.75. The head has a guide surface positioned longitudinally between the face and the body. The guide surface extends distally radially outward and forms an angle with the longitudinal axis in a range of 100° to 160°.

In another embodiment, an intravascular system includes a delivery catheter and a ring. The delivery catheter has a distal end and a proximal end. The delivery catheter also has an inner surface defining a lumen and an outer surface. The ring is affixed to the distal end of the delivery catheter and at least a part of the ring is positioned within the lumen. The ring includes a head having a face at a distal end of the ring and a body connected to the head and positioned proximally of the head with a longitudinal axis extending through the head and body. The face has a face radius and the body has a body radius. A face radius to body radius ratio is in a range of 1.20 to 1.75. The head has a guide surface positioned longitudinally between the face and the body. The guide surface extends distally radially outward and forms an angle with the longitudinal axis in a range of 100° to 160°.

In yet another embodiment, an intravascular system includes a delivery catheter, a ring, a connection arm, and a medical device. The delivery catheter has a distal end and a proximal end. The delivery catheter also has an inner surface defining a lumen and an outer surface. The ring is affixed to the distal end of the delivery catheter and at least a part of the ring is positioned within the lumen. The ring includes a head having a face at a distal end of the ring and a body connected to the head and positioned proximally of the head with a longitudinal axis extending through the head and body. The face has a face radius and the body has a body radius. The face radius is greater than a radius of the outer surface of the delivery catheter. A face radius to body radius ratio is in a range of 1.20 to 1.75. The head has a guide surface positioned longitudinally between the face and the body. The guide surface extends distally radially outward and forms an angle with the longitudinal axis in a range of 100° to 160°. The connection arm has a distal end and proximal end and the connection arm is connected to the ring at the proximal end and extends distally from the face of the ring. The medical device is connected to the distal end of the connection arm.

Additional features of embodiments of the disclosure will be set forth in the description which follows. The features of such embodiments may be realized by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIG. 3 is a side cross-sectional view of an embodiment of a conventional ring and delivery catheter system;

FIG. 4 is a side cross-sectional view of an embodiment of a ring and delivery catheter system, according to the present disclosure;

DETAILED DESCRIPTION

Figure 1:
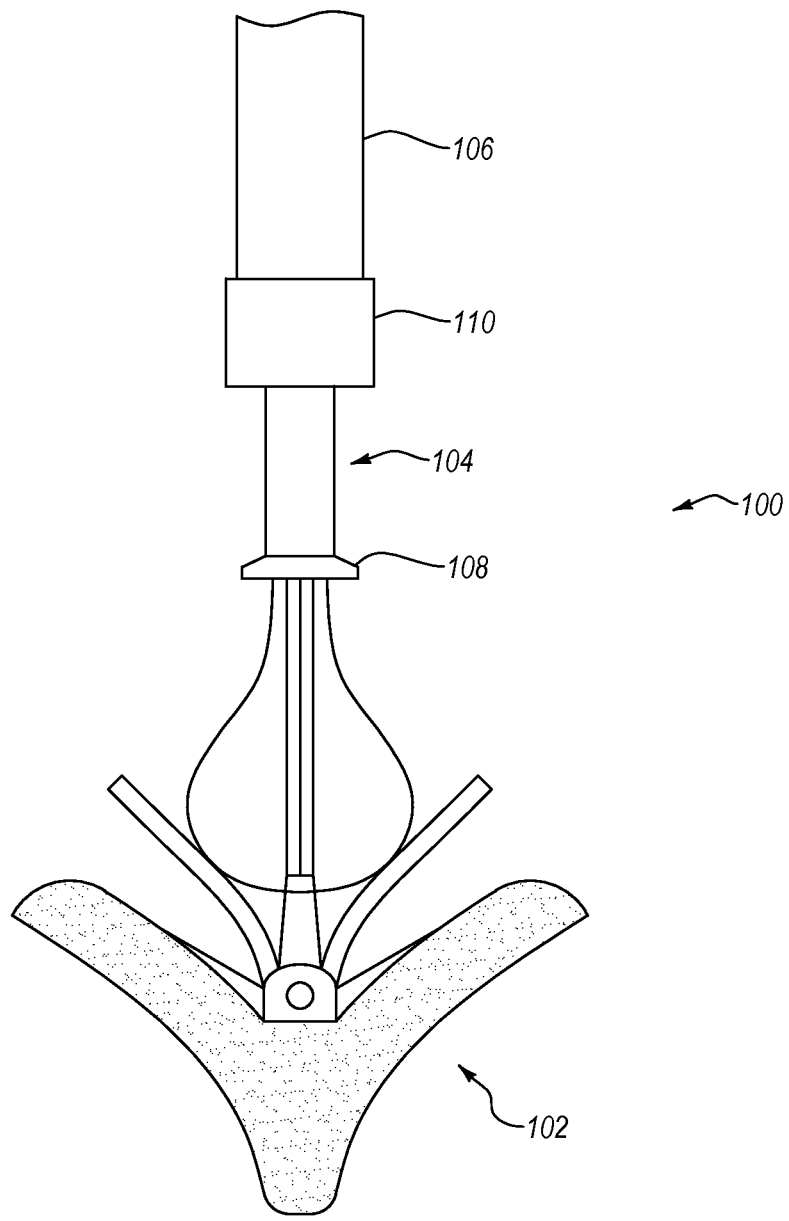
FIG. 1 depicts an embodiment of a heart valve repair clip connected to a distal end of a delivery catheter system, according to the present disclosure.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to manufacturing and using delivery catheter systems or other steerable catheters. A delivery catheter system may allow a medical professional to deliver an intravascular or other medical device to a target location in a patient's body. While the present disclosure will describe delivery catheter systems and applications thereof in relation to transvascular procedures in the heart, it should be understood that the devices, systems, and method described herein may be applicable to other bodily lumens and/or cavities. Additionally, elements described in relation to any embodiment depicted and/or described herein may be combinable with elements described in relation to any other embodiment depicted and/or described herein. For example, any element described in relation to an embodiment depicted in FIG. 4 may be combinable an embodiment described in FIG. 9.

A steerable guide catheter ("SGC") may be directed through a patient's vasculature and provide a steerable conduit through which a delivery catheter may pass. The delivery catheter may convey a medical device, such as a mitral valve repair clip, to a location in the patient's body. The delivery catheter may include one or more control wires extending through the delivery catheter to the medical device to control one or more moveable member thereon. The control wires may be directed through a ring having a plurality of passages therethrough. The ring may be positioned on a distal end of the delivery catheter and between the delivery catheter and the medical device. In some embodiments, the ring may be made of or include a radiopaque material to improve imaging of the ring and, hence, positioning of the ring in the patient's body.

The ring may have one or more features that facilitate and/or ease recapture of the medical device into the SGC. In some embodiments, the ring may have an outer diameter ("OD") greater than an OD of the delivery catheter. In other embodiments, the ring may have a sloped and/or curved surface adjacent an outer surface to guide the movement of the ring relative to the SGC. In yet other embodiments, the ring may have an OD greater than a width of the medical device. The ring may thereby allow for the medical device to be recaptured into the SGC by self-aligning within the SGC and substantially preventing the medical device contacting a distal tip of the SGC.

FIG. 1 depicts a valve repair system 100 according to at least one embodiment described herein. It should be understood that while the present description may disclosure features and elements in relation to a valve repair system 100, the features and elements described herein may be applicable to other intravascular devices and/or systems having other medical devices included therein. The valve repair system 100 may include a mitral clip 102, a delivery catheter 104 to which the mitral valve 102 is connected, and an SGC 106 through which the delivery catheter 104 may extend. The delivery catheter 104 may have a ring 108 located at a distal end thereof. In some embodiments, the ring 108 may have an OD that is larger than that of the delivery catheter 104. In other embodiments, the ring 108 may have an OD that is smaller than that of a SGC tip 110. The ring 108 may be configured to self-align concentrically within the SGC tip 110 and/or SGC 106. The ring 108 may be configured to align the mitral clip 102 with the SGC tip 110 and/or SGC 106 to facilitate recapture of the mitral clip 102.

Figure 2:
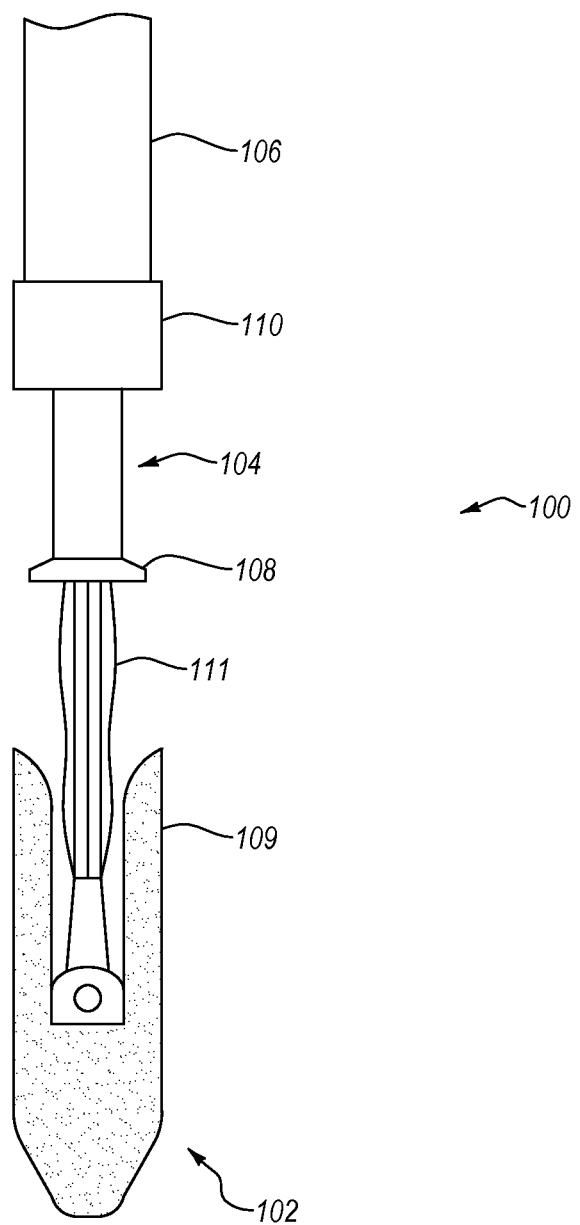
FIG. 2 depicts the heart valve repair clip and delivery catheter system of FIG. 1 during a partial recapture of the heart valve repair clip, according to the present disclosure.

FIG. 2 is a schematic representation depicting the collapse of the moveable arms 109 of the mitral clip 102 prior to recapture of the mitral clip 102 within the SGC tip 110 and/or SGC 106. The moveable arms 109 may be drawn inward from the expanded state depicted in FIG. 1 to the collapsed state depicted in FIG. 2. The one or more control wires 111 may apply a force to the moveable arms 109 to move the moveable arms 109 between the expanded state and the collapsed state. As shown in FIG. 2, the mitral clip 102 may have a lateral dimension greater than that of the delivery catheter 104 and/or the ring 108. The moveable arms 109 may, therefore, catch on the SGC tip 110 and/or SGC 106. The ring 108 may be configured to provide a reliable and robust alignment of the ring 108 and/or mitral clip 102 coaxially with and/or radially within the SGC 106. As used herein, "aligned coaxially" should be understood to mean sharing a common axis with another element, and, particularly in the present description, sharing a common longitudinal axis with another element. As used herein, "aligned radially within" should be understood to mean the first element (e.g., the ring 108) substantially centered within a transverse cross-section of the second element (e.g., the SGC 106). Aligning a first element coaxially with or radially within a second element may include the first element longitudinally overlapping the second element, but need not be so limited.

The ring 108 may be made of or include a radiopaque material to facilitate imaging of the ring 108 during an intravascular procedure. In at least one embodiment, the radiopaque ring 108 may be made of or include stainless steel. The stainless steel is visible during imaging, biocompatible, and weldable for connecting the ring 108 to a compression coil of the delivery catheter 104. In other embodiments, the ring 108 may include titanium, tungsten, barium sulfate, zirconium oxide, or combinations thereof. In yet other embodiments, the ring 108 may be made of or include a radiopaque polymer or a radiopaque material embedded in a polymer body.

FIG. 3 illustrates an embodiment of a conventional ring 212 in a conventional delivery catheter 204. The conventional ring 212 and conventional delivery catheter 204 may have substantially similar ODs, such that the conventional ring 212 is simply an extension of the conventional delivery catheter 204 that is guided through the SGC 206. However, the SGC 206 may be steered by a medical professional through tortuous vasculature in the patient's body and/or through a cavity in the patient's body. For example, the distal portion of the SGC 206 may have a radius of curvature one the scale of millimeters. The conventional delivery catheter 204 may include a resilient material. The resilient material may cause the conventional delivery catheter 204 to extend from the SGC 206 in a direction non-coaxial with the distal portion of the SGC 206. In such examples, retracting the conventional delivery catheter 204 into the SGC 206 may, similarly, move the conventional delivery catheter 204 in a direction non-coaxial with the distal portion of the SGC 206. The conventional delivery catheter 204 may not be centered within the SGC 206, causing the mitral clip 202 to contact and/or catch on the distal end of the SGC 206 inhibiting or substantially preventing recapture of the mitral clip 202 within the SGC 206.

FIG. 4 illustrates an embodiment of the ring 108 of FIG. 1 having an OD greater than that of the delivery catheter 104. The delivery catheter 104 may have an OD that is substantially similar to or smaller than the ID of the SGC 106 to allow the delivery catheter 104 to move freely within the SGC 106. The delivery catheter 104 may have an OD that is substantially similar to the ID of the SGC 106 to encourage the delivery catheter 104 to remain coaxial with the SGC 106 during the procedure, thereby providing greater control over the placement of the delivery catheter 104. The delivery catheter 104 may exit the distal portion of the SGC 106 more reliably and centered radially within the SGC 106. The delivery catheter 104 may also reenter the SGC 106 coaxially with the ring 108 centered radially relative to the SGC 106 and SGC tip 110.

The delivery catheter 104 may have an OD that is smaller than the ID of the SGC 106 to allow the delivery catheter 104 to move within the SGC 106 when the SGC 106 and delivery catheter 104 are moved through tortuous portions of the patient's vasculature. During movement through the tortuous portions of the patient's vasculature, the body of the delivery catheter 104 may contact the SGC 106. The friction therebetween may adversely affect the movement of the delivery catheter 104 within the SGC 106; limiting or substantially preventing deployment of the delivery catheter 140 from the SGC 106. A delivery catheter 104 having a smaller OD than the ID of the SGC 106 may provide more reliable control over longitudinal movement and rotational movement of the delivery catheter 104 within the SGC 106. The ring 108 of FIG. 4 allows the delivery catheter 104 and mitral clip 102 (or other medical device) to align coaxially and/or radially within the SGC 106 irrespective of the relative size of the delivery catheter 104 and SGC 106.

The delivery catheter 104 may define a lumen extending therethrough. At least a portion of the ring 108 may be positioned within the lumen of the delivery catheter 104 to connect the ring 108 to the delivery catheter. In some embodiments, the delivery catheter may contain a plurality of control wires that extend through the delivery catheter and into and/or through channels in the ring 108.

Figure 5:
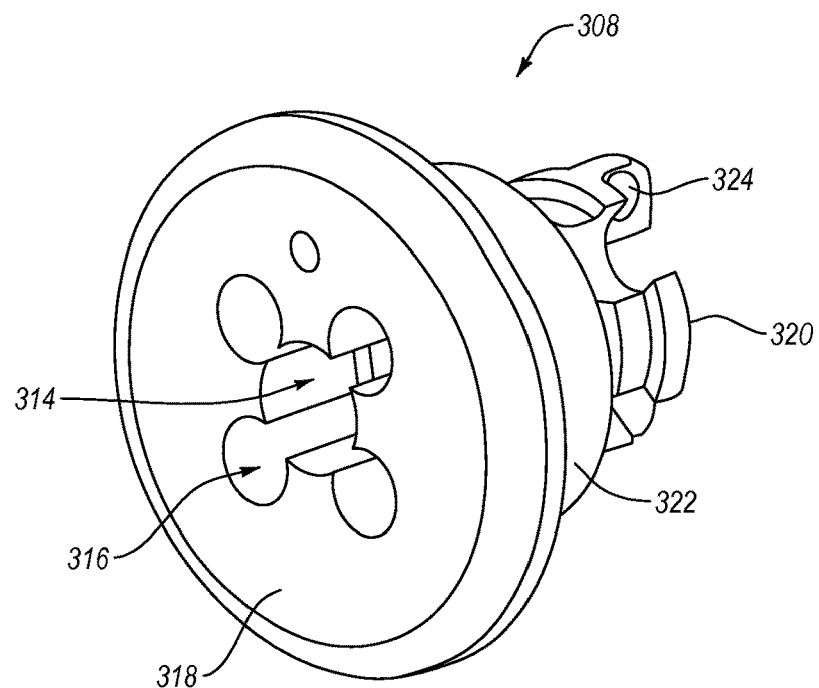
FIG. 5 is a distal perspective view of another embodiment of a radiopaque ring, according to the present disclosure.

FIG. 5 is a perspective view of an embodiment of a ring 308 according to the present disclosure. The ring 308 may have a major channel 314 that extends through at least a longitudinal portion of the ring 308. In at least one embodiment, the major channel 314 may extend through the entire longitudinal length of the ring 308. The major channel 314 may have a substantially circular transverse cross-section (e.g., be cylindrical). In other embodiments, the major channel 314 may have a transverse cross-section having another shape, such as square, octagonal, other polygonal, elliptical, irregular, or combinations thereof. In some embodiments, the major channel 314 may have a constant transverse cross-section along the length of the major channel 314.

The major channel 314 may have one or more minor channels 316 spaced about the major channel 314. In some embodiments, the one or more minor channels 316 may overlap at least a portion of the major channel 314, as shown in FIG. 5. In other embodiments, the one or more minor channels 316 may extend through a portion of the longitudinal length of the ring 308 without overlapping any portion of the major channel 314. In some embodiments, the one or more minor channels 316 may have a substantially circular transverse cross-section (e.g., be cylindrical). In other embodiments, the one or more minor channels 316 may have a transverse cross-section having another shape, such as square, octagonal, other polygonal, elliptical, irregular, or combinations thereof. In some embodiments, the one or more minor channels 316 may have a constant transverse cross-section along the length of the one or more minor channels 316.

The ring 308 may have a distal face 318 and a proximal base 320 at opposing longitudinal ends of a body 322. It should be understood that the terms "distal" and "proximal" are used herein as relative to a medical professional operating a heart valve repair system similar to that described herein. In other applications, the face 318 and the base 320 may be oriented in a different relative direction to an operator. The face 318 may be substantially flat, or may have a curved surface. The face 318 may be convex relative to the body 322, concave relative to the body 322, have another curve, or combinations thereof. The face 318 may be configured to complimentarily mate with a desired medical device or other interface component. The base 320 may extend away from the body 322 in a direction opposite that of the face 322. The base 320 may have one or more connection points 324 thereon to allow fixation of the ring 308 to a delivery catheter or other elongated member that provides communication between the ring 308 and a control system or operator outside the patient's body. In some embodiments, the ring 308 may have a single connection point 324. In other embodiments, the ring 308 may have a plurality of connection points 324. The plurality of connection points 324 may be distributed symmetrically about the base 320 such that any application of force to the connection points 324 may be applied to the ring 308 symmetrically.

Figure 6:
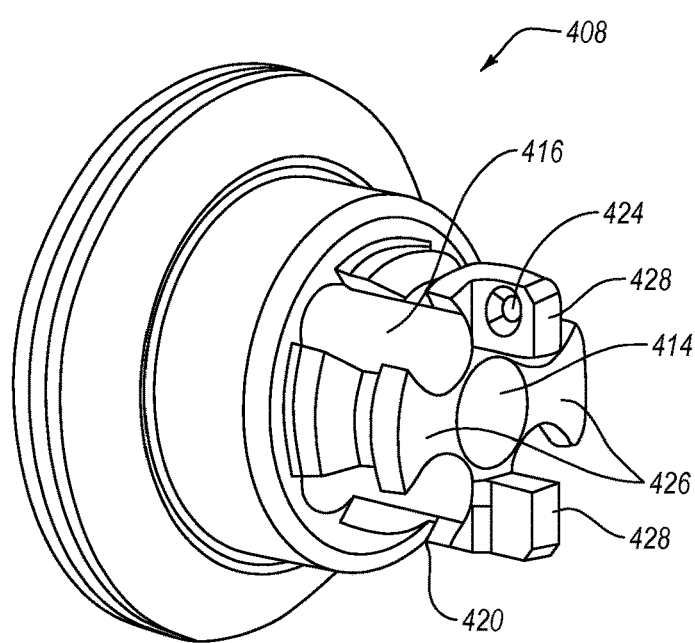
FIG. 6 is a proximal perspective view of yet another embodiment of a radiopaque ring, according to the present disclosure.

FIG. 6 illustrates a rear perspective view of an embodiment of a ring 408, according to the present disclosure. In some embodiments, the minor channels 416 of the ring 408 may substantially divide the base 420 into a plurality of posts 426. The plurality of posts 426 may be connected to the body 422. In some embodiments, the plurality of posts 426 may connect laterally to one another. In other embodiments, the plurality of posts 426 may not be connected to one another (e.g., the major channel 414 and plurality of minor channels 416 connect laterally to one another). In some embodiments, at least one of the posts 426 may have an extension 428 extending proximally therefrom. In embodiments having a plurality of extensions 428, the extensions may substantially radially oppose one another. As shown in FIG. 6, the plurality of extensions 428 may be space around and on opposite sides of the major channel 414. In at least one embodiment, one of the extensions 428 may have a connection point 424 thereon.

Figure 7:
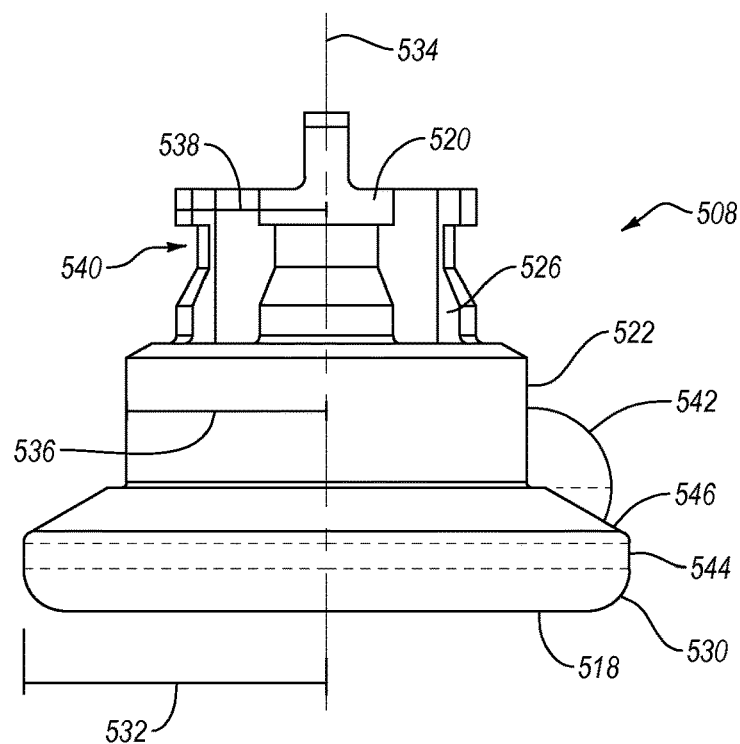
FIG. 7 is a side view of an embodiment of a radiopaque ring, according to the present disclosure.

FIG. 7 illustrates a side view of another embodiment of a ring 508 according to the present disclosure. The ring 508 may have a face 518 with a face edge 530 that defines a face radius 532. The face radius 532 may be measured from a longitudinal axis 534 of the ring 508 to a radial outermost point of the face 518 and face edge 530. The face edge 530 may, in some embodiments, be a curved edge. In other embodiments, the face edge 530 may be a beveled edge. In yet other embodiments, the face 518 may not have a face edge 530, and the face 518 may extend substantially flat to the radial outermost point of the ring 508. The face radius 532 may be greater than a body radius 536. The body radius 536 may be measured from the longitudinal axis 534 to the radial outermost point of the body 522. In some embodiments, the body radius 536 may be configured to substantially match an inner radius of a delivery catheter (e.g., the delivery catheter 104 described in relation to FIG. 1 and FIG. 2). In other embodiments, the body radius 522 may be larger than the inner radius of the delivery catheter. In some embodiments, the body 522 may include one or more engagement features to engage with an inner surface of the delivery catheter.

The face radius 532 and the body radius 536 may have a face-to-body ratio in a range having upper and lower values including any of 1.20, 1.25, 1.30, 1.35, 1.40, 1.45, 1.50, 1.55, 1.60, 1.65, 1.70, 1.75, or any value therebetween. For example, the face radius 532 and the body radius 536 may have a face-to-body ratio in a range of 1.20 to 1.75. In another example, the face radius 532 and the body radius 536 may have a face-to-body ratio in a range of 1.30 to 1.70. In yet another example, the face radius 532 and the body radius 536 may have a face-to-body ratio in a range 1.40 to 1.60. In at least one example, the face radius 532 and the body radius 536 may have a face-to-body ratio of 1.50.

The base 520 of the ring 508 may define a base radius 538 measured from the longitudinal axis 534 to a radial outermost point of the plurality of posts 526. In some embodiments, the base radius 538 may be the same or less than an inner diameter of a compression coil or other inner support member (e.g., hypotube) of the delivery catheter. The base radius 538 may also be larger than the inner diameter of a compression coil or other inner support member of the delivery catheter to provide a compression fit between the base 520 and the compression coil or other inner support member. The face radius 532 and the base radius 538 may have a face-to-base ratio in a range having upper and lower values including any of 1.60, 1.65, 1.70, 1.75, 1.80, 1.85, 1.90, 1.95, 2.00, 2.05, 2.10, 2.15, 2.20, 2.25, 2.30, or any value therebetween. For example, the face radius 532 and the base radius 538 may have a face-to-base ratio in a range of 1.60 to 2.30. In another example, the face radius 532 and the base radius 538 may have a face-to-base ratio in a range of 1.65 to 2.00. In yet another example, the face radius 532 and the base radius 538 may have a face-to-base ratio in a range 1.70 to 1.80. In at least one example, the face radius 532 and the base radius 538 may have a face-to-base ratio of 1.75.

The base 520 and the plurality of posts 526 therein may include a radial notch 540. In some embodiments, the notch 540 may include an inclined distal surface and a substantially transverse proximal surface as depicted in FIG. 7. In other embodiments, the notch 540 may include an inclined distal surface and an inclined proximal surface. In yet other embodiments, the notch 540 may include a substantially transverse distal surface and a substantially transverse proximal surface. The notch 540 may have a radial depth that is in a range having upper and lower values of 10% of the base radius 538, 15%, 20%, 25%, 30%, 35%, 40% of the base radius 538, or any value therebetween. For example, the notch 540 may have a radial depth in a range of 10% to 40% of the base radius 538. In another example, the notch 540 may have a radial depth in a range of 20% to 30% of the base radius 538. In at least one example, the notch 540 may have a radial depth of 25% of the base radius 538.

The ring 508 may have an angle 542 between the body 522 and a portion of a head 544 at or near the distal end of the ring 508. The angle 542 may define a guide surface 546 located longitudinally and/or laterally between the head 544 and the body 522. The angle 542 may be measured between the outer surface of the body 522 and the guide surface 546. The angle 542 may be an obtuse angle where the guide surface 546 slopes radially and distally (i.e., toward the face 518 of the head 544). The guide surface 546 may have an angle such that longitudinal movement of the ring 508 relative to SGC and/or SGC tip (such as SGC 106 and SGC tip 110 described in relation to FIG. 1 and FIG. 2) may convert at least a portion of a longitudinal compression force between the ring 508 and SGC and/or SGC tip to a transverse force. For example, the guide surface 546 may contact and/or interact with a distal edge of the SGC and/or SGC tip at apply a compressive force thereto. The compressive force may be applied between the guide surface 546 and the distal edge of the SGC and/or SGC tip at an angle to the longitudinal axis 534 of the ring 508, urging the ring 508 toward a radially centered position within the SGC and/or SGC tip.

In some embodiments of the ring 508, the guide surface 546 may be substantially flat in longitudinal cross-section. In other embodiments, the guide surface 546 may be at least partially curved in longitudinal cross-section. The guide surface 546 may be concave and/or convex relative to the head 544. In yet other embodiments, the guide surface 546 may be a combination of curved portions and flat portions in longitudinal cross-section. The angle 542 of the guide surface 546 relative to the longitudinal axis 534 of the ring 508 may be within a range having upper and lower values including any of 100°, 110°, 120°, 130°, 140°, 150°, 160°, or any value therebetween. For example, the angle 542 of the guide surface 546 may be in a range of 100° to 160°. In another example, the angle 542 of the guide surface 546 may be in a range of 110° to 140°. In yet another example, the angle 542 of the guide surface 546 may be 120°.

Figure 8:
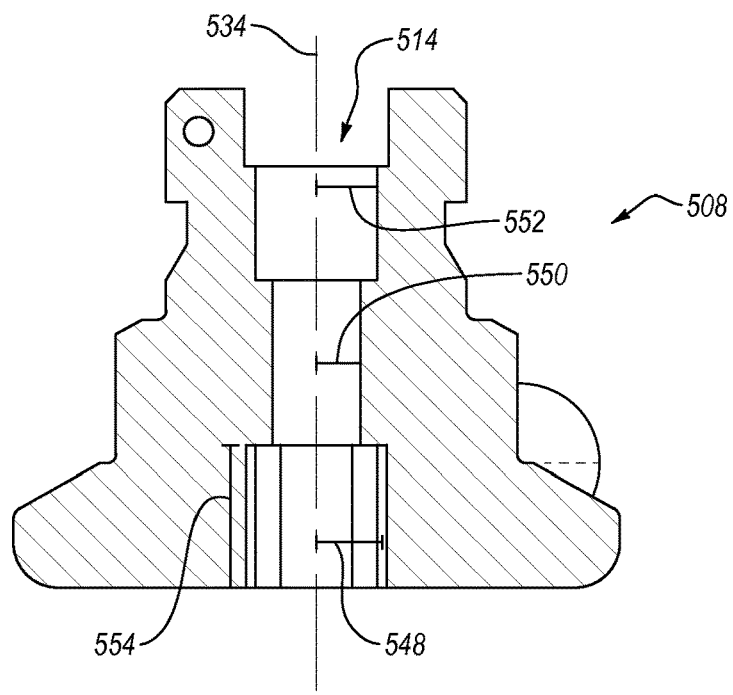
FIG. 8 is a side cross-sectional view of the radiopaque ring of FIG. 7.

FIG. 8 shows a longitudinal cross-section of the ring 508 of FIG. 7. The longitudinal cross-section shows the major channel 514 of the ring 508. As described herein, the major channel 514 may have a number of shapes in transverse cross-section, and while the size of the major channel 514 may be described in relation to a radius from the longitudinal axis 534 or diameter, the measurement of a radius should not be understood to limit the structure of part or the entire length of the major channel 514. In some embodiments, the major channel 514 may have a constant profile and/or radius in transverse cross-section along a longitudinal length thereof. In other embodiments, the major channel 514 may have a plurality of shapes and/or radii in transverse cross-section along a longitudinal length thereof. For example, the major channel 514 may have a distal radius 548, an intermediate radius 550, and a proximal radius 552. In some embodiments, the distal radius 548 may be greater than the intermediate radius 550. In other embodiments, the intermediate radius 550 may be less than the proximal radius 552. In yet other embodiments, the proximal radius 552 may be less than the distal radius 548 and the intermediate radius 550 may be less than the distal radius 548 and the proximal radius 552.

The major channel 514 may be configured to receive and substantially retain at least part of a connection arm therein. The connection arm and connection to the major channel 514 of the ring 508 will be described in more detail in relation to FIG. 11. Referring again to FIG. 8, the distal radius 548 of the major channel 514 may be configured to receive at least part of a connection arm. In some embodiments, the distal radius 548 may be configured to provide an interference fit with at least part of a connection arm. Similarly, the major channel 514 may have a distal portion 554 with a longitudinal length to receive at least part of a connection arm and retain the connection arm with substantial movement of the connection arm relative to the ring 508.

Figure 9:
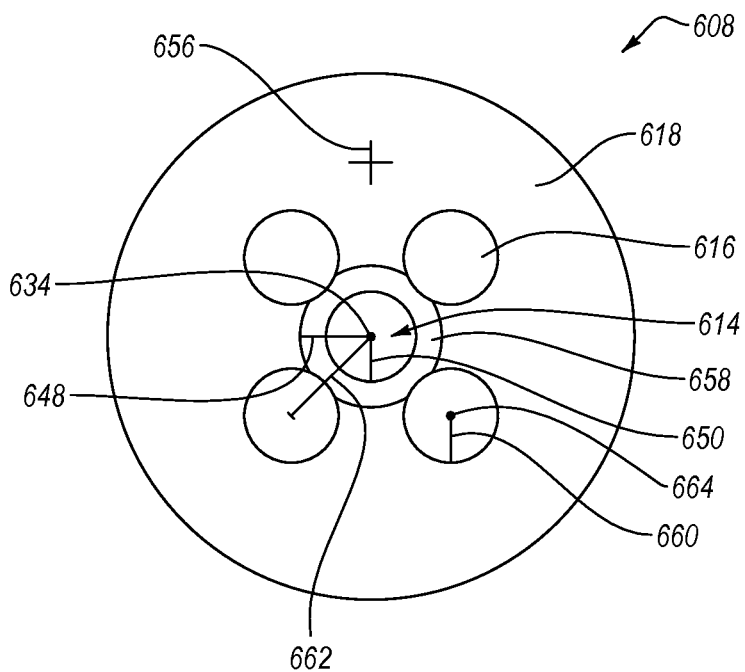
FIG. 9 is a distal end view of a further embodiment of a radiopaque ring, according to the present disclosure.

FIG. 9 is a distal view of an embodiment of a ring 608 according to the present disclosure. The ring 608 may have a major channel 614 and a plurality of minor channels 616. The face 618 of the ring 608 may include a visual indicator 656. In the depicted embodiment, the visual indicator 656 is a cross. In other embodiments, the visual indicator 656 may be a circle, a dot, a square, or any other identifiable shape that may render the face 618 of the ring 608 asymmetrical. As described herein, the major channel 614 and plurality of minor channels 616 may be distributed symmetrically about the longitudinal axis 634 of the ring 608. The ring 608 may otherwise exhibit one or more rotational symmetries (e.g., 180°, 120°, 90°, etc.). The visual indicator 656 may allow an operator to identify a particular orientation irrespective of other rotational symmetries of the ring 608. In some embodiments, the visual indicator 656 may be a recessed portion of the face 618. For example, the visual indicator 656 may be milled, stamped, or otherwise imprinted into the face 618 of the ring 608. In other embodiments, the visual indicator 656 may be a raised portion of the face 618. For example, the visual indicator 656 may be created on the face 618 by application of material thereto.

The distal view of FIG. 9 illustrates differences in a distal radius 648 and an intermediate radius 650 of the major channel 614. The transition between the distal radius 648 and the intermediate radius 650 in the major channel 614 may create a ledge 658 against which a connection arm may contact. The ledge 658 may be substantially annular. In some embodiments, the minor channels 616 may overlap with at least a portion of the major channel 614, such as in a distal portion of the major channel 614, and may overlap with at least part of the ledge 658.

A minor channel 616 may have a minor channel radius 660. In some embodiments, a minor channel 616 may have a constant minor channel radius 660 along the full longitudinal length of the minor channel 616. In other embodiments, the minor channel radius 660 may change over the longitudinal length of the minor channel 616. In some embodiments, all of the minor channels 616 may have substantially the same minor channel radius 660. In other embodiments, at least one of the minor channels 616 may have a different minor channel radius 660. The minor channels 616 may be positioned a minor channel distance 662 away from the major channel 614 in a transverse direction. For example, each minor channel 616 may have a minor longitudinal axis 664 that extends in the longitudinal direction and substantially parallel to the longitudinal axis 634 of the ring 608 and/or major channel 634. In some embodiments, the minor longitudinal axis 664 of each minor channel 616 may be an equal distance from the longitudinal axis 634 of the ring 608 and/or major channel 634. In other embodiments, the minor longitudinal axis 664 of at least one minor channel 616 may be a different distance from the longitudinal axis 634 of the ring 608 and/or major channel 634 as the minor longitudinal axis 664 of another minor channel 616.

Figure 10:
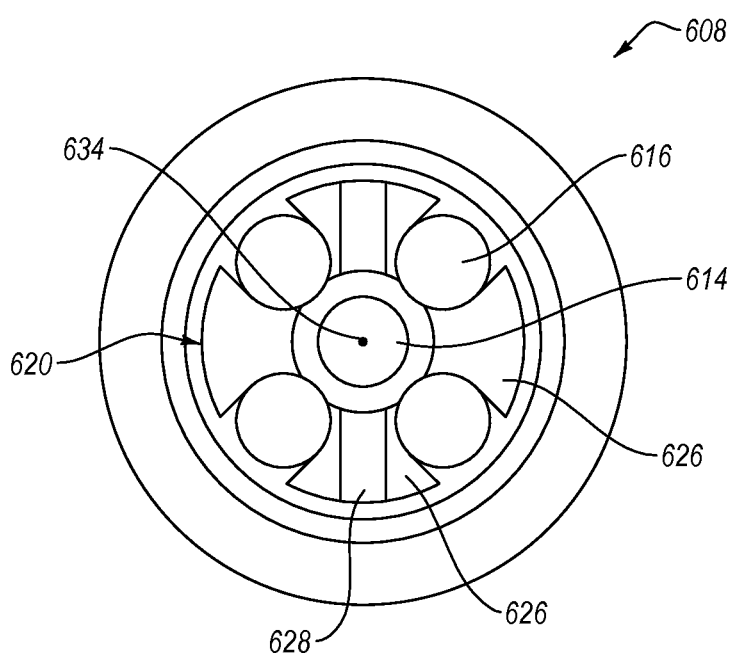
FIG. 10 is a proximal end view of the radiopaque ring of FIG. 9.

FIG. 10 illustrates a proximal view of the ring 608 of FIG. 9. As described herein, the plurality of minor channels 616 extending longitudinally through the base 620 may define a plurality of posts 626. The posts 626 may be further divided from one another by the major channel 614 located centrally to the posts 626. At least one of the posts 626 may have an extension 628 extending proximally therefrom. As shown in FIG. 10, an extension 628 may have a substantially constant lateral thickness irrespective of radial distance from the longitudinal axis 634 (i.e., having substantially parallel lateral surfaces). In other embodiments, the extension 628 may have other shapes in transverse cross-section. For example, the extension 628 may have non-parallel lateral surfaces and may taper toward the longitudinal axis 634, similar to the lateral surfaces of the posts 626, as illustrated in FIG. 10. In another example, the extension 628 may have non-parallel lateral surfaces and the extension may taper away the longitudinal axis 634.

As described herein, the extension 628 may have one or more connection points thereon to connect a wire thereto to limit or substantially prevent movement of the ring 608 relative to a delivery catheter. The extension 628 may also be configured to allow connection to a delivery catheter by a weld connection or other bonding of the extension material to a portion of the delivery catheter. For example, an extension 628 or other proximal portion of the ring 608 may be adhered to a body of the delivery catheter or to a support member of the delivery catheter, such as a compression coil. In at least one embodiment, the extension 628 may be laser welded to the compression coil of a delivery catheter. In other embodiments, an adhesive material may be applied between at least part of the ring 608 and the delivery catheter.

Figure 11:
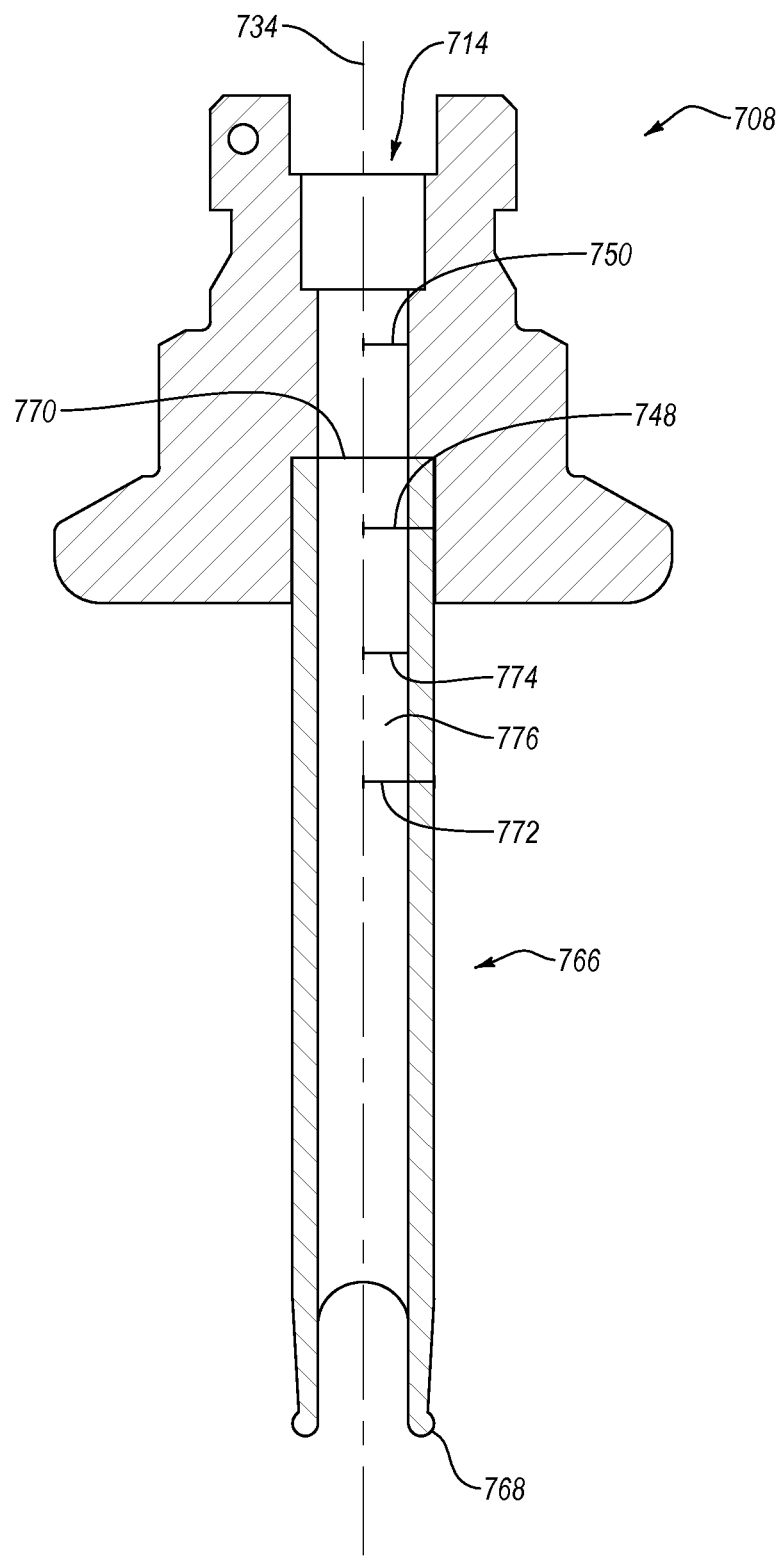
FIG. 11 is a side cross-sectional view of a radiopaque ring having a connection arm connected thereto, according to at least one embodiment described herein.

FIG. 11 illustrates a side cross-sectional view of an embodiment of a ring 708 having a connection arm 766 extending distally therefrom. The connection arm 766 may have a distal end 768 configured to retain and/or grip a medical device (e.g., a mitral clip) and a proximal end 770 configured to connect to the ring 708. In some embodiments, the proximal end 770 may be configured to fit in the major channel 714 with an interference fit therein. The interference fit between the distal radius 748 of the major channel 714 and the OD 772 of the connection arm 766 may be sufficient to limit or substantially prevent movement of the connection arm 766 relative to the ring 708. In other embodiments, additional reinforcement of the connection therebetween may be provided by an adhesive material between the ring 708 and the connection arm 766. In yet other embodiments, the connection between the ring 708 and the connection arm 766 may include welding, brazing, or otherwise bonding the material of the connection arm 766 to the material of the ring 708.

A medical device may be retained on the connection arm 766 by a wire or other elongate member extending through the major channel 714 and the connection arm 766 to the medical device. The connection arm 766 may have an ID 774 defining a central bore 776 extending therethrough. The central bore 776 may be coaxial with the longitudinal axis 734 of the ring 708 and/or major channel 714. The ID 774 of the connection arm 766 may be substantially the same as the intermediate radius 750. In some embodiments, the central bore 776 and major channel 714 may provide a channel having a substantially continuous inner surface.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A device for aligning components of an intravascular system, the device comprising:
   a head having a face at a distal end of the device, the face having a face radius;
   a body connected to the head and positioned proximally of the head, the body having a body radius wherein a ratio of the face radius to the body radius is in a range of 1.20 to 1.75;
   a base connected to the body and positioned proximally of the body;
   a guide surface positioned on the head and longitudinally between the face and the body, the guide surface extending distally radially outward and forming an angle with an outer surface of the body in a range of 100° to 160°; and
   a major channel and a plurality of minor channels extending longitudinally from the distal end to the base, the plurality of minor channels communicating with the major channel in the head and being separated from the major channel in the base.

2. The device of claim 1, further comprising a radiopaque material.

3. The device of claim 1, wherein the plurality of minor channels are distributed radially about the major channel.

4. The device of claim 1, wherein the guide surface extends from a radial outermost point of the head to a radial outermost point of the body.

5. The device of claim 1, wherein the device is made of stainless steel.

6. The device of claim 1, further comprising a plurality of posts extending from the body.

7. The device of claim 1, further comprising a plurality of connection points.

8. The device of claim 1, wherein the head and the body are integrally formed.

9. The device of claim 1, wherein the head and the body form a unitary ring.

* * * * *